(12) United States Patent
Ogawa et al.

(10) Patent No.: US 7,479,267 B2
(45) Date of Patent: Jan. 20, 2009

(54) CELL-OR ORGAN-DIFFERENTIATION CONTROLLERS AND METHOD OF CONTROLLING MORPHOGENESIS BY USING THE SAME

(75) Inventors: Kenichi Ogawa, Okayama (JP); Kenji Henmi, Okayama (JP); Yasushi Tasaka, Sapporo (JP)

(73) Assignee: Okayama Prefecture, Okayama-Ken (JP)

( * ) Notice: Subject to any disclaimer, the term of this patent is extended or adjusted under 35 U.S.C. 154(b) by 791 days.

(21) Appl. No.: 10/258,234

(22) PCT Filed: Apr. 24, 2001

(86) PCT No.: PCT/JP01/03491

§ 371 (c)(1),
(2), (4) Date: Oct. 22, 2002

(87) PCT Pub. No.: WO01/80638

PCT Pub. Date: Nov. 1, 2001

(65) Prior Publication Data

US 2003/0110527 A1 Jun. 12, 2003

(30) Foreign Application Priority Data

Apr. 25, 2000 (JP) .............................. 2000-123761

(51) Int. Cl.
*A01N 25/00* (2006.01)
(52) U.S. Cl. ..................................... 424/9.2; 504/116.1
(58) Field of Classification Search ............. 504/116.1, 504/188, 326, 339, 186
See application file for complete search history.

(56) References Cited

U.S. PATENT DOCUMENTS

| 4,361,436 | A | * | 11/1982 | McCarthy et al. | ........... 504/128 |
| 4,436,547 | A | * | 3/1984 | Sampson | .................... 504/136 |
| 5,869,456 | A | * | 2/1999 | Levy et al. | ..................... 514/19 |
| 6,030,950 | A | | 2/2000 | Ohlenschlager | ............... 514/18 |

FOREIGN PATENT DOCUMENTS

| FR | 2710234 | 3/1995 |
| JP | 59-106407 | 6/1984 |
| JP | 4-217608 | 8/1992 |
| JP | 5-49470 | 3/1993 |
| JP | 2000-38308 | 2/2000 |
| WO | WO 91/00008 | 1/1991 |
| WO | WO 00/05969 | 2/2000 |

OTHER PUBLICATIONS

Peter J. Lea. "Primary Nitrogen Metabolism". Chapter 7 in Plant Biochemistry. Dey and Harborne, eds. p. 305-306. 1997.*
Farm Chemicals Handbook. 1995 edition. p. C214, "Kazoe".*
Kurepa et al 1998 The Plant Journal 14(6): 759-764.*
Sanchez-Fernandez et al 1997 Proc. Natl. Acad. Sci. USA 94: 2745-2750.*
Reese et al 1987 Plant Physiology 84: 574-577.*
O. Tanaka, et al., "Effect of Ferricyanide, Ferrocyanide and KCN on Growth and Flowering in the Short-Day Plant *Lemna paucicostata* 6746", *Plant and Cell Physiol.*, vol. 24, No. 4, pp. 705-711, 1983.
R. Macknight, et al., "FCA, a Gene Controlling Lowering Time in *Arabidopsis*, Encodes a Protein Containing RNA-Binding Domains", *Cell*, vol. 89, pp. 737-745, 1997.
N. Wada, et al., "Flower Induction by Polyamines and Related Compounds in Seedlings of Morning Glory (*Pharbitis nil* cv. Kidachi)", *Plant Cell Physiol.*, vol. 35, No. 3, pp. 469-472, 1994.
P. B. Applewhite, et al., "A role for spermidine in the bolting and flowering of *Arabidopsis*", *Physiologia Plantarum*, vol. 108, pp. 314-320, 2000.
K. C. Kim, et al., "Photoperiodic Floral Induction in *Pharbitis* Cotyledons Affected by Polyamines and Ethylene", *J. Plant Biol.*, vol. 38, No. 3, pp. 227-234, 1995.
E. Tarenghi, et al., "Polyamines, floral induction and floral developments of strawberry (*Fragaria ananassa* Duch.)", *Plant Growth Regulation*, vol. 17, pp. 157-165, 1995.
T. Potikha, et al., "The Involvement of Hydrogen Peroxide in the Differentiation of Secondary Walls in Cotton Fibers", *Plant Physiology*, vol. 119, pp. 849-858, 1999.
R. Sanchez-Fernandez, et al., "Cell proliferation and hair tip growth in the *Arabidopsis* root are under mechanistically different forms of redox control", *Proc. Natl. Acad. Sci.*, vol. 94, pp. 2745-2750, 1997.
B. Earnshaw, et al., "The Effect of Glutathione on Development in Wild Carrot Suspension Cultures", *Biochemical and Biophysical Research Communications*, vol. 133, No. 3, pp. 988-993, 1985.
B. Earnshaw, et al., "Control of Wild Carrot Somatic Embryo Development by Antioxidants[1]—A Probable Mode of action of 2,4-Dichlorophenoxyacetic Acid", *Plant Physiol.*, vol. 85, pp. 273-276, 1987.
K.P. Reddy, et al., "Catalase activity in rice shoot apex during panicle initiation", *Plant and Cell Physiology*, vol. 26, No. 7, pp. 1419-1424, 1985.
Z. Ye, et al., "The developmental transition to flowering represses ascorbate peroxidase activity and induces enzymatic lipid peroxidation in leaf tissue in *Arabidopsis thaliana*", *Plant Biology*, vol. 1999, p. 75, 1999.
Z. Ye, et al., "The developmental transition to flowering represses ascorbate peroxidase activity and induces enzymatic lipid peroxidation in leaf tissue in *Arabidopsis thaliana*", *Plant Science*, vol. 158, No. 1-2, pp. 115-127, 2000.
J. Kurepa, et al., "Oxidative stress tolerance and longevity in *Arabidopsis*: The late-flowering mutant gigantea is tolerant to paraquat", *Plant Journal*, vol. 14, No. 6, pp. 759-764, 1998.

(Continued)

Primary Examiner—David H Kruse
(74) Attorney, Agent, or Firm—Wenderoth, Lind & Ponack, L.L.P.

(57) ABSTRACT

A method of regulating flowering of a plant by applying an effective amount of a substance that affects the synthesis or amount of glutathione in cells to the plant and cultivating the plant under conditions suitable for growth.

6 Claims, 10 Drawing Sheets

OTHER PUBLICATIONS

O. Fontaine et al., "Dormancy breakage of *Hordeum vulgare* seeds: Effects of hydrogen peroxide and scarification on glutathione level and glutathione reductase activity", *Plant Physiology and Biochemistry*, vol. 32, No. 5, pp. 677-683, 1994.

M.E.B. Naredo et al., "Responses to seed dormancy-breaking treatments in rices species", *Seed Science and Technology*, vol. 26, No. 3, pp. 675-689, 1998.

C. Chien et al., "Mechanism of hydrogen peroxide in improving the germination of *Cinnamomum camphora* seed", *Seed Science and Technology*, vol. 22, No. 2, pp. 231-236, 1994.

S. Gallais et al., "Pyridine nucleotides and redox charges during germination of non-dormant and dormant caryopses of *Avena sativa L*", *Journal of Plant Physiology*, vol. 153, No. 5-6, pp. 664-669, 1998.

K. Ogawa et al., "A mechanism for promoting the germination of *Zinnia elegans* seeds by hydrogen peroxide", *Plant and Cell Physiology*, vol. 42, No. 3, pp. 286-291, 2001.

L. Liu et al., "Localization of hydrogen peroxide production in *Zinnia elegans* L. Stems", *Phytochemistry*, vol. 52, No. 4, pp. 545-554, 1999.

H. Fukuda, "Tracheary element differentiation", *Plant Cell*, vol. 9, No. 7, pp. 1147-1156, 1997.

A. Groover et al., "Programmed cell death of plant tracheary elements differentiating in vitro", *Protoplasma*, vol. 196, No. 3-4, pp. 197-211, 1997.

* cited by examiner

CELL-OR ORGAN-DIFFERENTIATION CONTROLLERS AND METHOD OF CONTROLLING MORPHOGENESIS BY USING THE SAME

This application is a U.S. national stage of PCT/JP01/03491 filed Apr. 24, 2001.

TECHNICAL FIELD

The present invention is related to a method of regulating or controlling the differentiation of cells or organs, more specifically, to a method of regulating the differentiation of cells or organs using a substance capable of regulating the reduction-oxidation state of cells, and an agent for regulating the differentiation of cells or organs comprising such a substance.

BACKGROUND ART

All of individual organisms are built up via the differentiation and development (morphogenesis) of cells and/or organs. For example, in a multicellular organism, cells are assembled to form tissues and/or organs, which are then intricately combined to form individuals. Cells must differentiate and be organized in a manner specific to respective tissue or organ so that each tissue or organ can exert their peculiar functions.

It is thought that cells operate their genetic programs under the control of a regulator such as hormone that cells receive in the process of the differentiation and development of cells and organs. It is known that the concentration gradient of a regulator in the morphogenesis stage such as germination governs the organ differentiation in Amphibia such as newt. Also, in Drosophila, the related genes have been sought by isolating a variant having mutation in the regulation system. In plants, it is known that a regulator referred to as a plant hormone regulates or controls development of a plant. As described above, a specific regulator(s) participates in developments of individual organism.

Recently, the homology of genes functioning in a genetic program related to development among all has become attract a good deal of attention.

Also, it is known that all of organisms are greatly affected by certain kinds of stresses (for examples, light, temperature, chemicals, etc.) imposed during the development and/or morphogenesis process.

From the high homology predicted in genetic programs related to development and also the community of factors causing stress (light, temperature, chemicals, etc.) among organisms, it is suggested that there exist a common substance among organisms which is involved in the genetic transmittance system leading to the said genetic program. However, it has not been reported that such a substance was isolated or identified yet.

It has been thought that a substance capable of controlling the differentiation of cells and organs of all or wide range of organisms would greatly contribute to development of research and industry.

DISCLOSURE OF INVENTION

One of objects of the present invention is to provide a means for regulating the differentiation of cells and organs.

Another object of the present invention is to establish a means of controlling the flowering time of plants, the redifferentiation from callus, and the like, using an agent for regulation (regulator).

The present inventors have found that, among stress-related factors which affect development and/or morphogenesis, a substance regulating the reduction-oxidation (hereinafter, referred to as "redox") state of cells and existing commonly among organisms can affect the differentiation and development of cells and organs, and achieved the present invention.

The present invention provides an agent for regulating the differentiation of cells or organs, which comprises a regulator for redox state of cells.

BRIEF DESCRIPTION OF DRAWINGS

BSO treatment was started 12 days after imbibition of seeds (FIG. 1A, fca and FIG. 1B, Ler). As to fca, BSO treatment was also started on day 17 (FIG. 1C). In the graphs, 23 cont and 4 cont are the results obtained without or with cold treatment, respectively (control experiments). The values are expressed as mean±standard error.

BSO treatment was started 12 days after germination. Glutathione was given concurrently with BSO treatment. In this figure, 23 cont and 4 cont have the same meanings as in FIGS. 1A and B show the results for Ler and for fca, respectively.

FIG. 9 provides photographs showing the regulating effect of hydrogen peroxide on the morphological alteration of *Zinnia elegans* (Regulation of Development (2)). The concentration of hydrogen peroxide used in the treatment (unit: mM) is shown at the right downside of each panel. The figures show plants at 48 hours after imbibition. As the concentration of hydrogen peroxide used in the treatment increased, the cotyledon opening occurred rather than root elongation during the germination. From the figure showing the germination where treatment was conducted with 60 mM hydrogen peroxide, it can be observed that the cotyledon opening happened earlier and cotyledons come out from the pericarp before roots come out.

BEST MODE FOR CARRYING OUT THE INVENTION

As used herein, the phrase "differentiation of cells or organs" has the meanings widely known in the filed of biology, which generally means a process where cells or organs are structurally and functionally specialized. In regard to plants, specific examples of "differentiation of cells or organs" include floral formation, morphogenesis at the time of germination, defoliation including the abscission layer formation, winter bud formation, dormancy breakage, pollen germination, embryogenesis including fertilization process, redifferentiation from callus, tracheary element formation, root hair formation, trichome formation, and the like. In regard to animals, specific examples include nerve cell differentiation or dendrite formation thereof, formation of epidermal cell or tissue, gamete formation, ovum development including fertilization, blood cell differentiation, germinative cell formation, and the like. As for Mycota, examples include sporophyte formation or perforating hyphae formation; as for Protista, examples include ontogenesis, flagellum formation or differentiation of a cell organelle; as for bacteria, specific examples include colony formation, flagellum formation or spore formation. However, the present invention is not limited to these examples.

The present invention also includes differentiation and development of cell organelles such as plastid, mitochondrion and so on are.

With reference to the present invention, the term "development" refers to the process where an individual is formed from organism-constituting units (e.g., molecules and cells), in other words, the morphogenesis at the molecular and cellular levels.

Accordingly, biological individuals, which are the subjects (objects) of "regulation of differentiation of cells or tissues", "regulation of development" and so on, include all the multi- and uni-cellular organisms involving development (formation from units for organism configuration). That is, the subjects of the present invention are Plantae including flowering plant, lichens and bryophyte, and Animalia including echinoderm, arthropod, mammalian and so on. The present invention also includes uni-cellular organisms as far as the shape is concerned.

Throughout the specification, the phrase "the reduction-oxidation (redox) state of cells" means a condition estimated on the basis of the following indices: tendency to generate active oxygens; the absolute amount of glutathione; the ratio of reduced glutathione to oxidized glutathione (GSH/GSSG); the absolute amount of reduced form of nicotinamide-adenine dinucleotide phosphate (NAD(P)H); the ratio of NADPH/NADP$^+$; the ratio of oxidized form/reduced form of cytochrome c; the ratio of reduction-oxidation of components in electron transport chains, such as plastoquinone and ubiquinone.

Substances regulating the reduction-oxidation state in organism are known in the art, and therefore the present invention is not limited to the above.

The phrase, "reduction-oxidation (redox) state regulator of cells" refers to a substance which has an activity to change the above-mentioned value and includes, for example, a substance affecting the synthesis or amount of glutathione, a substance promoting or inhibiting the generation of active oxygens and a substance promoting or inhibiting the conversion of a compound into either of oxidized- or reduced form.

The "redox-state regulator of cells" used in the present invention may be any substance(s) having the above-mentioned activity. Specific examples include, but not limited to, active oxygen species such as hydrogen peroxide and superoxide anion radical; antioxidant enzymes such as superoxide dismutase, catalase, ascorbate peroxidase, dehydroascorbate reductase, monoascorbate reductase, glutathione reductase and glutathione peroxidase; glutathione synthesis inhibitors such as buthionine sufoximine and methionine sulfoximine; glutathione derivatives such as reduced glutathione, oxidized glutathione, homoglutathione, carboxypropylglutathione and dicarboxyethylglutathione; respiratory inhibitors such as paraquat, KCN and NaN$_3$; polyamines such as putrescine, spermine and spermidine; and a starting material or an inducer which gives rise to the above-mentioned substances in a cell.

The agent of the present invention for regulating the differentiation of cells or tissues (hereinafter, it may be referred to as a "differentiation regulator") consists of at least one redox-state regulator or comprises a redox-state regulator(s) and a suitable carrier(s) or an excipient(s). Such a preparation can be obtained according to a known method by mixing a redox-state regulator with pharmaceutically acceptable carrier, pharmaceutical additives, and the like. The preparation can be formulated in any form, including solution, emulsion and solid, depending on the subject or method of application.

In some cases, the rate and state of development can be easily controlled by combining two or more species of redox-state regulators as active ingredients. Such ingredients to be combined may be selected, for example, from substances which function in the same metabolic system but exert opposite effect. In the working Examples below, the flowering time of a plant is regulated by combined use of glutathione and glutathione inhibitor BSO. Any combinations of substances acting on different metabolic system are also available.

When the present differentiation regulator includes two or more species of redox-state regulators, active ingredients may be present in one preparation, or be formulated separately so that they can be used simultaneously or sequentially.

The present invention also provides a method for regulating development of an organism, which comprises applying the above-mentioned differentiation regulator to an organism having an altered sensitivity to the regulator, and the resultant organism. As used herein, the term "organism having an altered sensitivity" refers to an organism of which sensitivity to a specific substance has been changed, such as the mutant fca having an altered sensitivity to BSO compared to the wild-type plant Ler. Such individuals can be naturally occurring or made artificially.

The present differentiation regulator is applicable to every organism sensitive to a regulator of redox state of cells, which is an active ingredient. In the case of plants, the regulator has effect on both of the dicots and monocots of angiosperm.

When the present differentiation regulator comprising as an active ingredient a redox-state regulator of cells is applied to a plant as the subject, and when it is intended to, for example, regulate artificially flowering, regeneration of individual from callus or tracheary element differentiation, germination etc., such objective would be achieved through the regulation of redox state of cells, especially the generation level of active oxygens, the synthesis and redox ratio of glutathione, and the like. Additionally, it is thought that the morphogenesis of a plant, such as root hair formation or trichome formation can be regulated by the above-mentioned substance capable of regulating the redox state of cells.

Thus, according to the present method, it is possible to regulate a broad range of development of plants. The optimal condition for regulating development is not fixed, and varies depending on kinds and/or morphological features and the like of plants, and also on the intended purpose.

Typical examples of plants to which the present differentiation regulator applicable include the followings. Convolvulaceae such as *Pharbitis* (*Pharbitis nil Choisy*), *Calystegia* (*Calystegia japonica Choisy, Calystegia hederacea* and *Calystegia soldanella* Rohm. et Schult.), *Ipomoea* (*Ipomoea pes-caprae* and *Ipomoea batatas* Lam. var. *edulis Maikno*) and *Cuscuta* (*Cuscuta japonica Chois.* and *Cuscuta australis*) Caryophyllaceae such as *Dianthus* (*Dianthus caryophillus* L.), *Stellaria, Minuartia, Cerastium, Sagina, Arenaria, Moehringia, Pseudostellaria, Hankenya, Spergula, Spergularia, Silene, Lychnis, Melandryum* and *Cucubalus* Casuarinaceae, Saururacea, Piperaceae, Choranthaceae, Sailicaceae, Myricaceae, Juglandaceae, Betulaceae, Fagaceae, Ulmaceae, Moraceae, Urticaceae, Podostemaceae, Proteaceae, Olacaceae, Santalaceae, Loranthaceae, Aristolochiaceae, Rafflesiaceae, Balanophoraceae, Polygonaceae, Chenopodiaceae, Amaranthaceae, Nyctaginaceae, Cynocrmbaceae, Phytolaccaceae, Aizoaceae, Portulacaceae, Magnoliaceae, Trochodendraceae, Cercidphyllaceae, Nymphaeaceae, Ceratophyllaceae, Ranunculaceae, Lardizabalaeae, Berberidaceae, Menispermaceae, Calycanthaceae, Lauraceae, Papaveraceae, Capparidaceae, Cruciferae, Droseraceae, Nepenthaceae, Crassulaceae, Saxifragaceae, Pittosporaceae, Hamamelidaceae, Platanaceae, Rosaceae, Leguminosae, Oxalidaceae, Geraniaceae, Linaceae, Zygophyllaceae, Rutaceae, Cimaroubaceae, Meliaceae, Polygalaceae, Euphorbiaceae, Callitrichaceae, Buxaceae, Empetraceae, Coriariaceae, Anacardiaceae, Aquifoliaceae, Celastraceae, Staphyleaceae, Icacinaceae, Aceraceae, Hippocastanaceae, Sapindaceae, Sabiaceae, Balsaminaceae, Rhamnaceae, Vitaceae, Elaeocarpaceae, Tiliaceae, Malvaceae, Stearculiaceae, Actinidiaceae, Theaceae, Guttiferae, Elatinaceae, Tamaricaceae, Violaceae, Flacourtiaceae, Stachyuraceae, Passifloraceae, Begoniaceae, Cactaceae, Thymelaeaceae, Elaegnaceae, Lythraceae, Punicaceae, Rhizophoraceae, Alangiaceae, Melastomataceae, Hydrocaryaceae, Oenotheraceae, Haloragaceae, Hippuridaceae, Araliaceae, Umbelliferae, Cornaceae, Diapensiaceae, Clethraceae, Pyrolaceae, Uricaceae, Myrsinaceae, Primulaceae, Plumbaginaceae, Ebenaceae, Symplocaceae, Styracaceae, Oleaceae, Loganiaceae, Gentianaceae, Apocynaceae, Asclepiadaceae, Polemoniaceae, Boraginaceae, Verbenaceae, Labiatae, Solanaceae, Scrophulariaceae, Bignoniaceae, Pedaliaceae, Orobanchaceae, Gesneriaceae, Lentibulariaceae, Acanthaceae, Myoporaceae, Phrymaceae, Plantaginaceae, Rubiaceae, Caprifoliaceae, Adoxaceae, Valerianaceae, Dipsacaceae, Cucurbitaceae, Campanulaceae, Compositae and so on.

Typical examples of monocotyledoneae plants include the followings. Lemnaceae such as *Spirodela* (*Spirodela polyrhiza Schleid*) and *Lemna* (*Lemna paucicostata* and *Lemna trisulca*), Orchidaceae such as *Cattleya, Cymbidium, Dendrobium, Phalaenopsis, Vanda, Paphiopedilum and Oncidium*, Typhaceae, Sparganiaceae, Potamogetonaceae, Najadaceae, Scheuchzeriaceae, Alismataceae, Hydrocharitaceae, Triuridaceae, Gramineae, Cyperaceae, Palmae, Araceae, Eriocaulaceae, Commelinaceae, Pontederiaceae, Juncaceae, Stemonaceae, Liliaceae, Amaryllidaceae, Dioscoreacea, Iridaceae, Musaceae, Zingiberaceae, Cannaceae and Burmannia.

As described above, in the present invention, "the reduction-oxidation (redox) state" of a certain organism is affected by a substance common to a broad range of animals and plants. For examples, glutathione, which is an important factor determining the "redox state" is ubiquitous in organisms, and the glutathione synthesis pathway and the proteins controlled by glutathione share high homology among organisms. Furthermore, the enzymes related to active oxygens have high homology among organisms. Therefore, the redox-state regulator of the present invention is useful in the regulation of development of organisms such as animals as well as plants.

Such a regulator can be used in, but not limited to, the induction of parthenogenesis or differentiation of cells or tissues such as nerve or epidermis, restoration of differentiated tissues such as dendrites, differentiation of cells such as immunocompetent cells, formation of a zygote or a sporogenesis, formation of flagellum, and the like.

Examples of organisms of animal kingdom include Vertebrata, Echinodermata, Protochordata, Coelenterata, Mollusca, Arthropoda, Annelida, Porifera, Platyhelminthes and so on. Furthermore, the organisms include fungi (e.g., basidiomycete and ascomycete) which perform sporophyte formation, and microorganisms such as procaryote (e.g., actinomycete) which perform sporogenesis, and yeast when the present invention is aimed at budding and zygote, but are not limited to the above examples.

Examples of application of the present regulator include a medicine used for repairing skin from burn injury or for recovery from nerve damage; control of mushroom cultivation; equalization of quality of Pisces by parthenogenesis; preservation of the freshness of flowers etc.; prevention of infection through the inhibition of appressorium formation of pathogenic bacterium etc. The present invention is not limited to the above.

The present differentiation regulators are used for a variety of organism individuals, organs, tissues or cells by an appropriate method depending on the dosage form. For example, when the regulator is a solution or emulsion and the organism potential to differentiate cells and organs is a plant, the regulator can be dispersed, dropped or painted on not only the growth point, but also a portion such as stem, leaf etc. or whole entity of the plant. When the regulator is a solid or powder, it can be absorbed from soil via the root. If the organism potential to differentiate cells and organs is a waterweed such as floating grass, the regulator can be used as an additive to the bottom bed so as to be absorbed by roots. Further, the regulator in the solid form can be dissolved into water gradually. The present invention can be applied by any methods and is not restricted to the above use.

When the differentiation regulator is an additive to the bottom bed or a solid preparation, example of the career(s) generally includes solid careers, such as minerals (talc, clay, vermiculite, diatomite, kaolin, calcium carbonate, calcium hydrate, terra alba, silica gel etc.), flour, starch, and the like. When the regulator is a solution, examples of the career(s) generally includes liquid careers, such as water, aromatic hydrocarbons such as xylene etc., alcohols such as ethanol, ethylene glycol etc., ketones such as acetone etc., ethers such as dioxane, tetrahydrofuran etc., dimethylformamide, dimethyl sulfoxide, acetonitrile, and the like.

Furthermore, the present differentiation regulator may include an appropriate additive (coadjuvant). Examples of additives include anionic surfactant such as alkyl sulfate esters, alkylsulfonate salts, alkylarylsulfonate salts, dialkylsulfosuccinate salts and the like, cationic surfactant such as higher aliphatic amine salts and the like, nonionic surfactant such as polyoxyethylene glycol alkyl ether, polyoxyethylene glycol acyl ester, polyoxyethylene glycol polyalcohol acyl ester, cellulose and so on, thickener such as gelatin, casein, gum arabic and so on, extender, binder, and the like.

If necessary, a plant growth regulator such as benzoic acid, nicotinic acid, nicotinic-acid amide, pipecolic acid, and so on can be incorporated into the formulations within the limits of not diminishing the intended effect of the present invention.

Although the present invention is exemplified mainly with regard to regulation/control of flowering time, a person skilled in the art will understand that the regulation of development can be effected in other biological systems according to the teachings in the present specification.

Treatment with a differentiation regulator can be performed by applying an appropriate concentration of a redox-state regulator of cells before the initiation of and/or during an ordinary cultivation of a seed or a callus of a plant of interest. Usually, the application of a regulator would be more effective when it is conducted concurrently with treatment adapted to the nature of the subject plant (e.g., long-day, short-day, and the like). Such treatment is known to those skilled in the art. For example, in the case of a relative long-day plant such as Eustoma grandiflorum, as described in the aftermentioned Examples, it would be advantageous to use the present differentiation regulator under lightening at higher level of illumination intensity.

Therefore, the present invention encompasses the use of a differentiation regulator in any plant growing methods usually employed in the art.

The differentiation regulator may consist of an active ingredient, i.e., redox-state regulator; however, it is preferably formulated in a suitable dosage form applicable to individual plants, such as solutions, solids, powders, emulsions and bottom bed additives. Such preparations can be prepared according to a known method by admixing an agent for regulating the redox state of cells as an active ingredient with carrier components, pharmaceutical additives, and so on, which are known to be pharmaceutically acceptable in the art, within the limits of not diminishing the effect for regulating flowering time.

The following examples further illustrate the present invention in more details, however, these examples should not be construed as limiting the scope of the present invention.

EXAMPLE 1

Regulation of Flowering Time (1)

Arabidopsis thaliana late-flowering mutant fca (Accession No. N167) obtained from Arabidopsis Stock Center publicly established at the University of Nottingham (U.K.) and wild type plant Ler (Accession No. NW20) were grown at 23° C. under a day length condition of 16-h light/8-h dark cycle at 100 μE/m² light intensity and used in the experiments. As a medium, soil consisting of 2 Vermiculite (Asahi Kogyo), 2 Kureha molding for raising seedlings (KUREHA chemical industry Co., Ltd.) and 1 Vermiculite (Asahi Kogyo), which are stacked in layer as the lower, middle and the upper layers, respectively, was used.

As a redox-state regulator of cells, L-buthionine sulfoximine (BSO), which is a glutathione synthesis inhibitor, and glutathione were used in combination.

Figure 1:
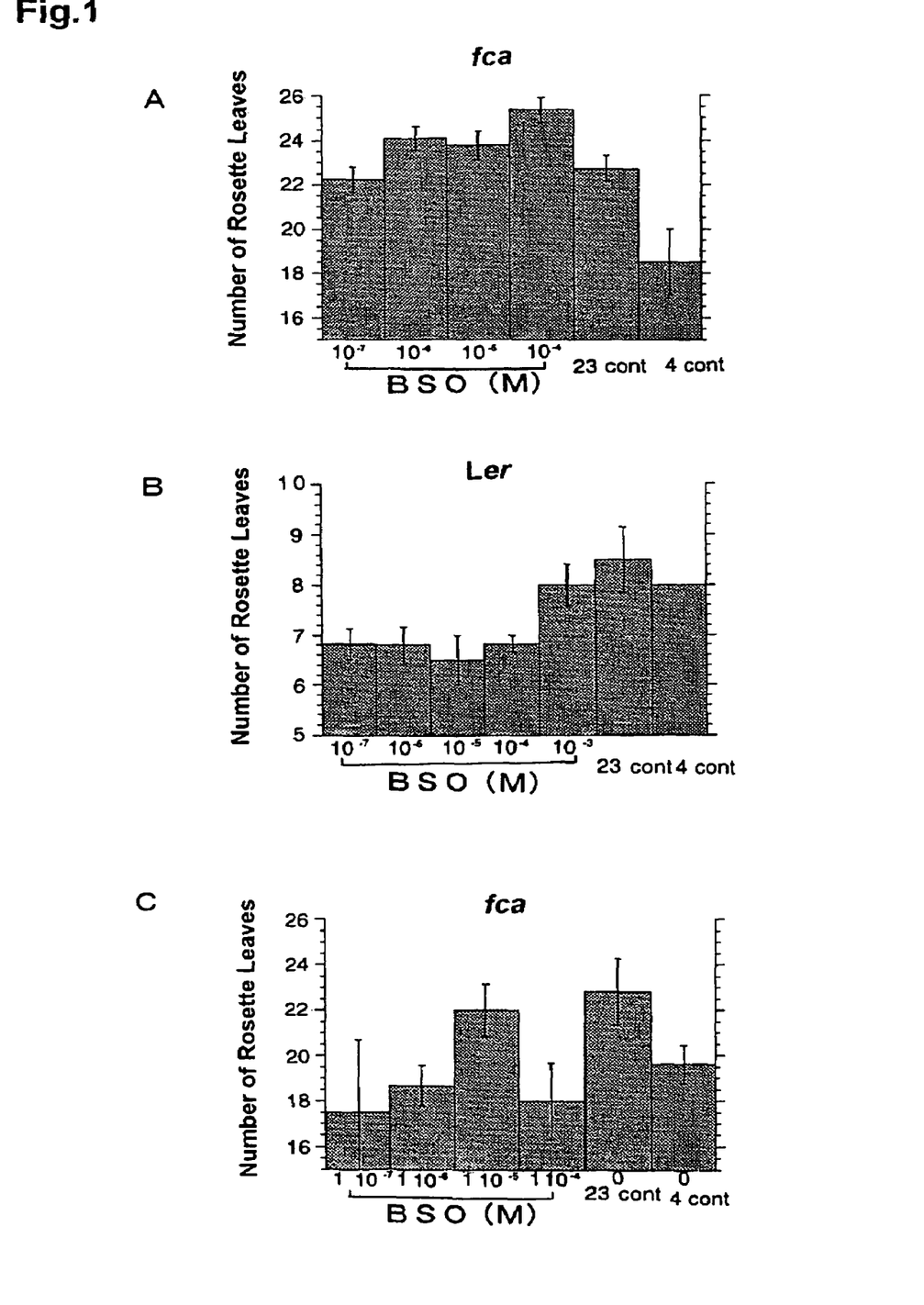
FIG. 1 provides graphs showing the regulating effect of a glutathione inhibitor, L-buthionine sulfoximine (BSO), on the flowering time of Arabidopsis thaliana late-flowering mutant fca (hereafter referred to as "fca") or wild-type plant Ler (hereafter referred to as "Ler"). The regulatory effect was evaluated on the basis of the number of rosette leaves.
Figure 2:
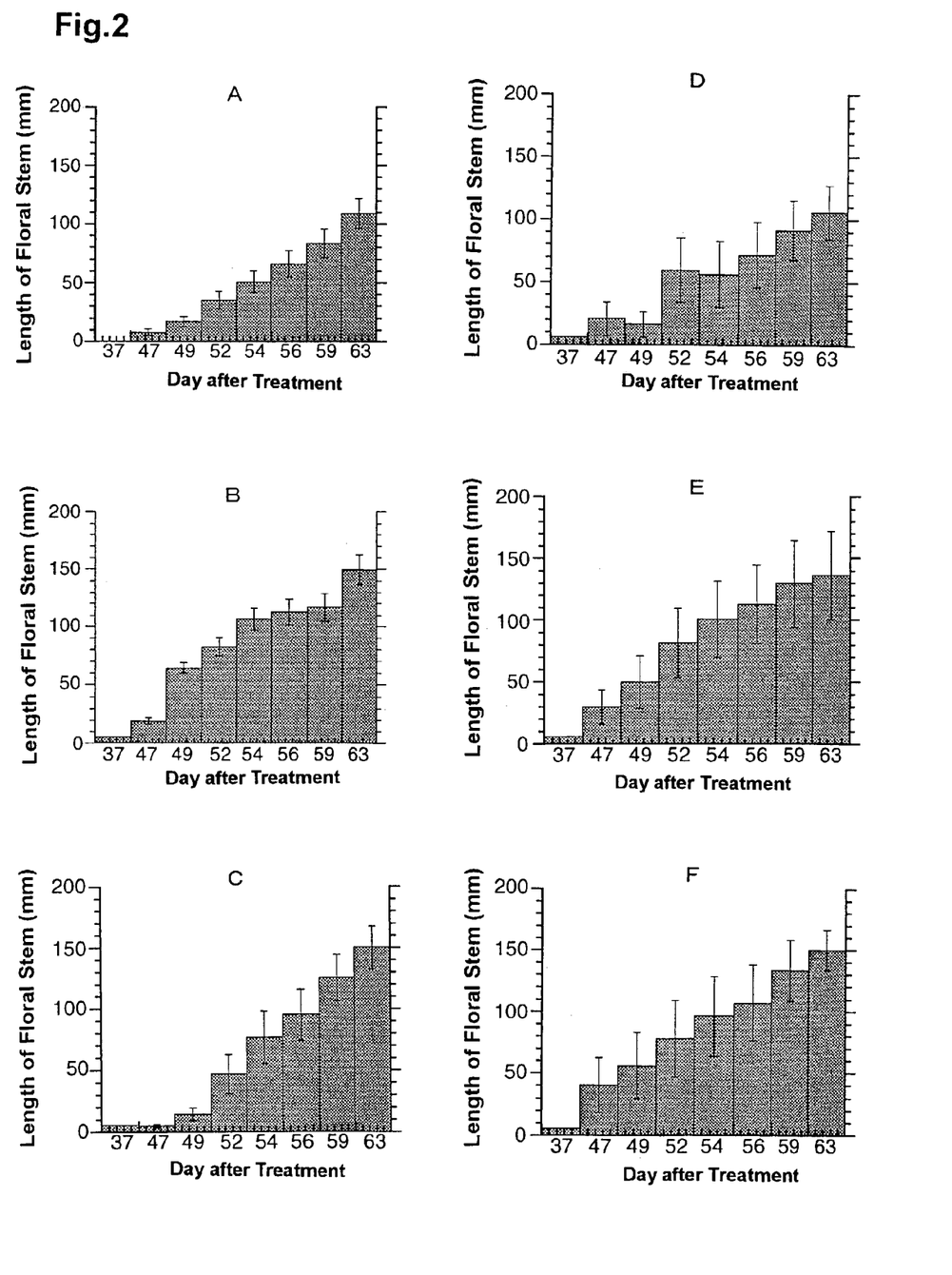
FIG. 2 provides graphs showing the regulating effect of BSO on the elongation rate of fca floral stem. BSO treatment was started 17 days after germination and the effect on the elongation (growth) of floral stem was examined. BSO concentration used for treatment was as follows: A, 0 M; B, $10^{-7}$ M; C, $10^{-6}$ M; D, $10^{-5}$ M; E, $10^{-4}$ M; and F, $10^{-3}$ M. The values are expressed as mean±standard error.
Figure 3:
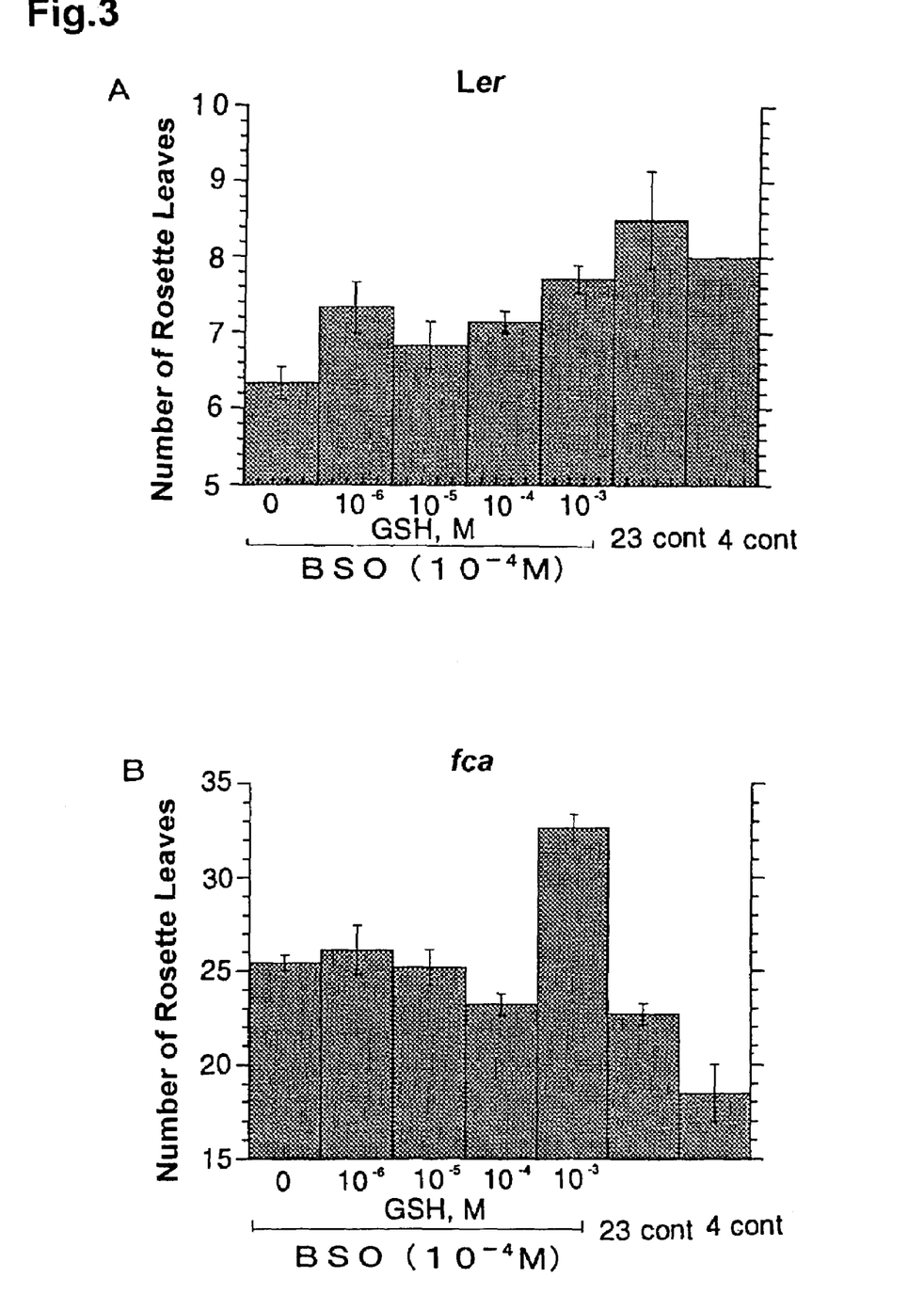
FIG. 3 provides graphs showing the effect of glutathione (GSH) on flowering (the transition to flowering) time-regulating effect of BSO.

BSO Treatment:

BSO was dissolved in water at a final concentration of $10^{-1}$M and used as a stock solution. Then, the treatment solutions at $10^{-3}$-$10^{-7}$M were prepared from the stock solution (FIGS. 1-3). Two to three plants were placed per a pot (about 40×50 mm) and the treatment solution was added dropwise around the shoot apex at 5 ml/day per a pot. The treatment was performed on day 0 (the initiation date of treatment), 1, 3, 5 and 7, which set of treatments was regarded as one processing.

Glutathione Treatment:

Glutathione treatment was performed after dissolving glutathione into the BSO solution at a concentration of $10^{-4}$ M.

The effect of treatment was estimated based on the number of rosette leaves and the elongation rate of floral stem. The results are shown in FIGS. 1-3. In these figures, the 23 cont and 4 cont are the results obtained without or with cold treatment, respectively (control experiments). Cold treatment was performed at 4° C. concurrently with a chemical treatment. In FIG. 2, BSO concentrations used for treatment were as follows: A, 0 M; B, $10^{-7}$ M; C, $10^{-6}$ M; D, $10^{-5}$ M; E, $10^{-4}$ M; and F $10^{-3}$ M. The values are expressed as mean±standard error.

(1) The fca plants, on 17 days after imbibition, were treated with the glutathione synthesis inhibitor BSO. The result at 1 week afterward is shown in FIG. 1C. It is shown that, after 1 week from treatment, flower bud was recognized with naked eye and the rosette leaf number decreased compared with the water treated control group. The elongation rate of floral stem was also monitored for several months after treatment (FIG. 2). As shown in FIG. 2, the elongation rate of floral stem in the treated group is faster than that of control group, indicating that flowering was accelerated. The result showing a decrease in the rosette leaf number indicates that BSO treatment accelerated not only the growth rate after the transition to flowering but also the determination of the transition to flowering itself.

(2) The fca plants, on 12 days after imbibition, were treated with the glutathione synthesis inhibitor BSO. The result of 1 week later is shown in FIG. 1A. Contrary to (1) above, FIG. 1A shows that the treatment delayed the flowering time of fca. On the other hand, when the wild type Ler was subjected to the same experiment, treatment started 12 days after imbibition significantly accelerated the transition to flowering (FIG. 1B). When Ler was grown in an agar medium containing BSO just after germination, the bolting was delayed, similarly to the case where fca was treated with a differentiation regulator at earlier stage, initiating on 12 days after imbibition.

(3) BSO treatment and glutathione (GSH) treatment was concurrently performed. BSO solution (concentration: $10^{-4}$ M) to which glutathione was added was used in the same manner as described above.

The plants treated at the time when BSO treatment delays the transition to flowering showed acceleration of the transition to flowering as GSH concentration increased first; however, showed delay of the transition to flowering at 1 mM (FIG. 3B). On the other hand, the plants treated at the time when BSO treatment accelerates the transition to flowering showed the delay of the transition to flowering as GSH concentration increased (FIG. 3A).

These results indicate that glutathione, glutathione synthesis inhibitor or a combination thereof can control the flowering time and further the elongation rate of floral stem. Additionally, these results revealed that it is necessary to adjust the time (stage) of treatment depending on cultivar.

EXAMPLE 2

Regulation of Flowering Time (2)

*Arabidopsis thaliana* late-flowering mutant fca was grown in a manner similar to that described in Example 1 at 23° C. under the day length condition of 16-h light/8-h dark cycle at 100 µE/m²/s light intensity and used in the experiments.

Figure 4:
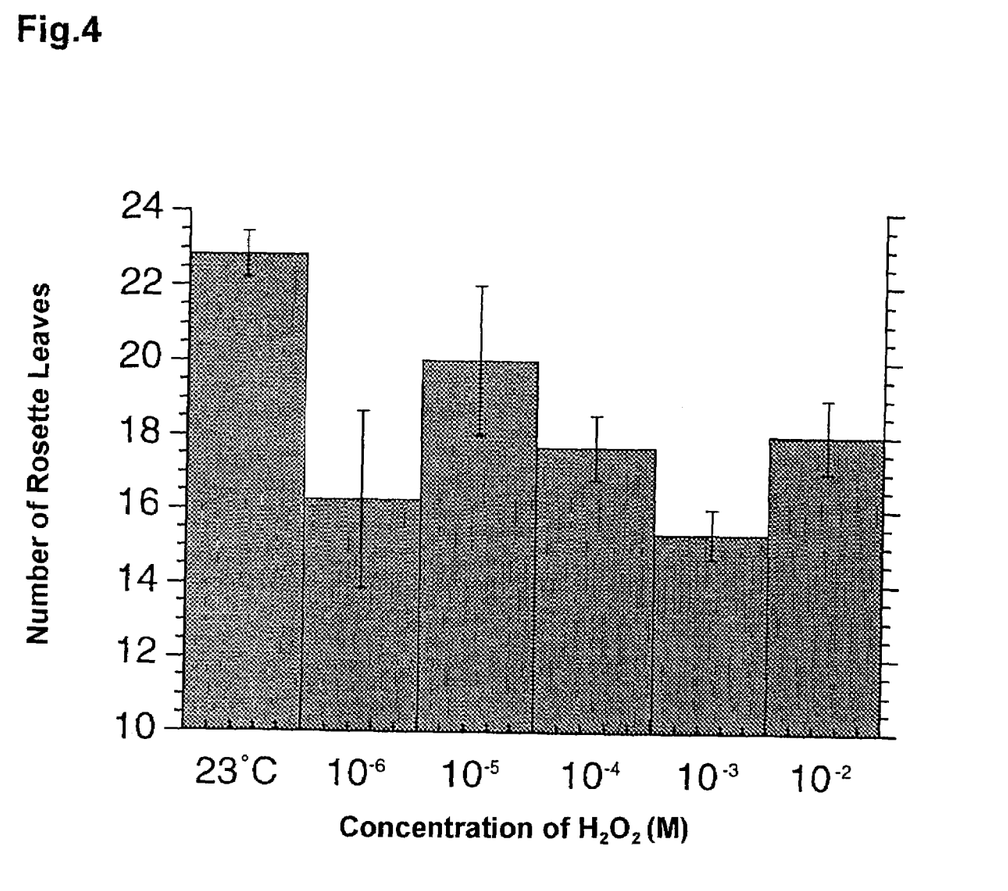
FIG. 4 is a graph showing the regulating effect of hydrogen peroxide on the flowering time of late-flowering mutant fca. Hydrogen peroxide treatment was started 17 days after imbibition of seed. The column "23° C." shows the result of water treatment (control experiment). The values are expressed as mean±standard error.

As a redox-state regulator of cells, hydrogen peroxide was used at the concentrations indicated in FIG. 4. An aqueous solution of hydrogen peroxide was prepared immediately before use. Two to three plants were placed per a pot (about 40×50 mm). On 17 days after imbibition and thereafter, the treatment solution was added dropwise around the shoot apex at 5 ml/day per a pot. The treatments were performed on day 0 (the initiation date of treatment), 1, 3, 5 and 7, which set of treatments was regarded as one processing. The time of floral transition was compared using the rosette leaf number as an index. The results are shown in FIG. 4. In the figure, the 23 cont is the result of water treatment (control experiment). The values are expressed as mean±standard error.

Figure 5:
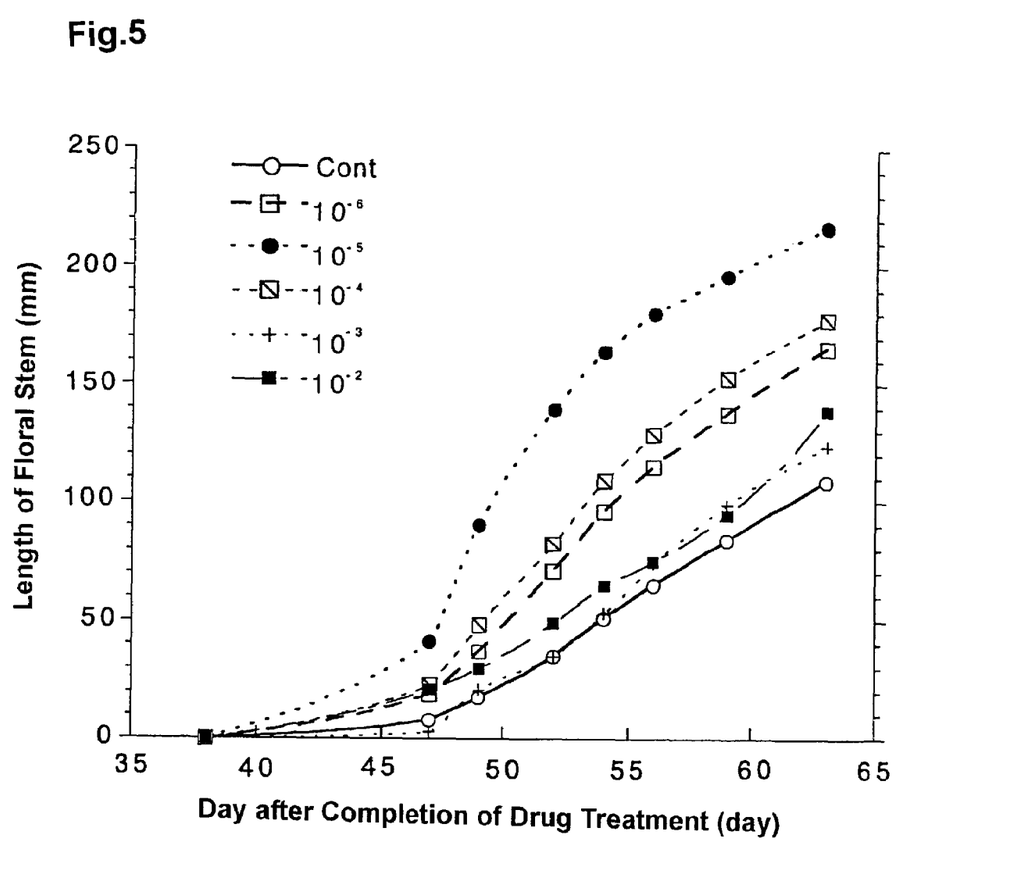
FIG. 5 is a graph showing the regulating effect of hydrogen peroxide on the elongation rate of fca floral stem. Hydrogen peroxide treatment was started 17 days after germination and the effect on the elongation of floral stem was examined. The concentration of hydrogen peroxide used in the treatment is shown on the top of the figure. The values are expressed as mean±standard error.

The time of floral transition based on the rosette leaf number was accelerated in the treated plants at every concentrations compared with the control plants treated with water (FIG. 4). Also, the elongation rate of floral stem was accelerated at the optimum concentration ($10^{-5}$M) (FIG. 5). In FIG. 5, the transverse axis shows the day after the completion of the agent treatment.

The above results indicate that active oxygens itself and substances which generate active oxygens have the effect of regulating floral transition time and accelerating the elongation rate of floral stem.

EXAMPLE 3

Regulation of Flowering Time (3)

*Arabidopsis thaliana* late-flowering mutant fca was grown in a manner similar to that described in Example 1 at 23° C. under a day length condition of 16-h light/8-h dark cycle at 100 µE/m² light intensity and used in the experiments.

Figure 6:
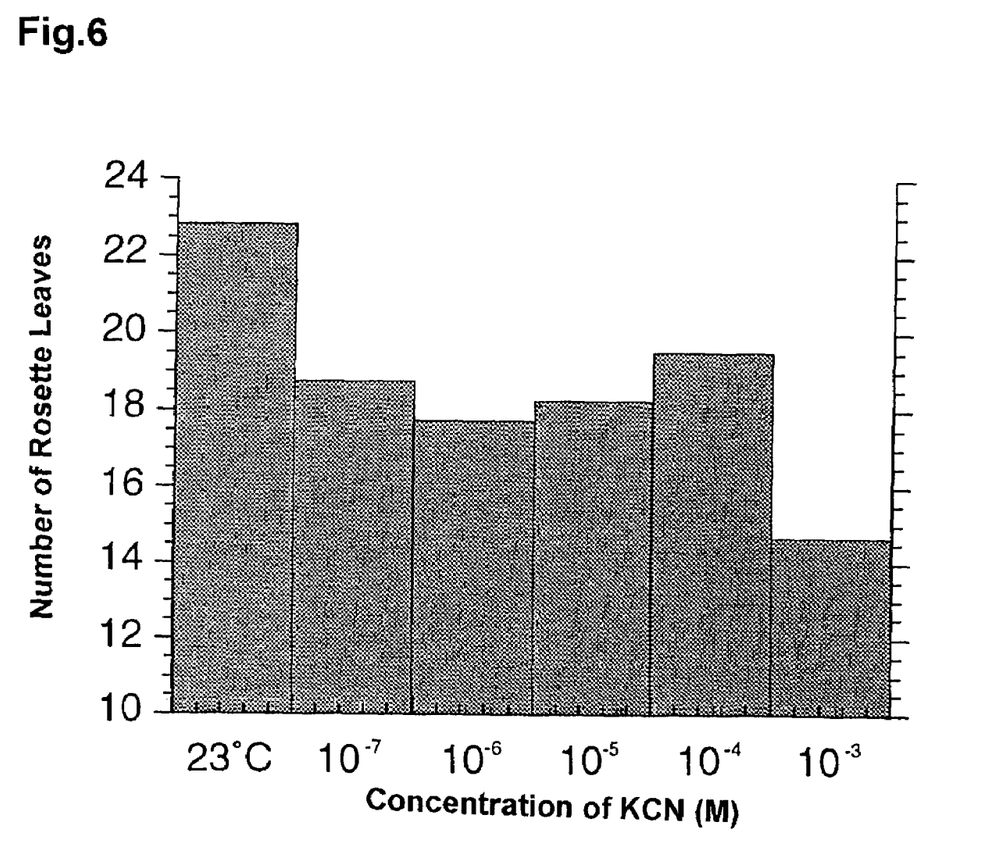
FIG. 6 is a graph showing the regulating effect of potassium cyanide (KCN) on the flowering time of a late-flowering mutant fca. KCN treatment was started 17 days after imbibition of seed. The column "23° C." shows the result of water treatment (control experiment). The values are expressed as mean±standard error.
Figure 7:
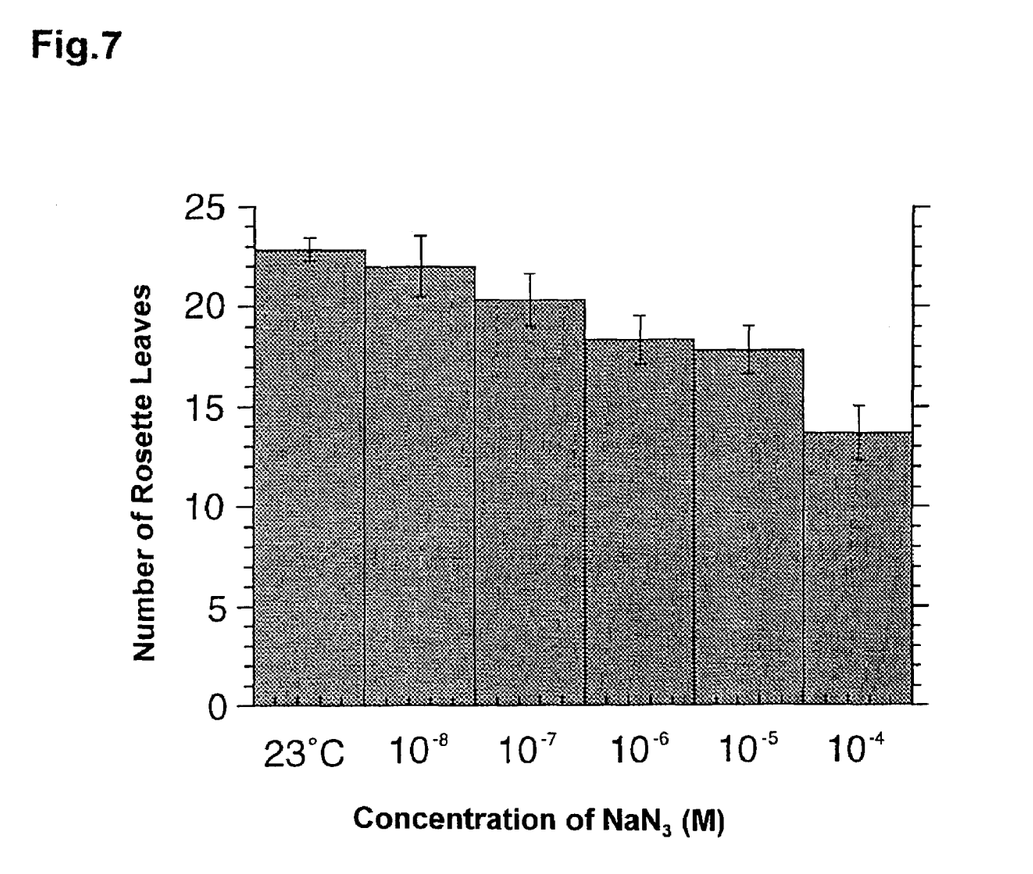
FIG. 7 is a graph showing the regulating effect of sodium azide ($NaN_3$) on the flowering time of a late-flowering mutant fca. Sodium azide treatment was started 17 days after imbibition of seed. The column "23 cont" shows the result of water treatment (control experiment). The values are expressed as mean±standard error.

As a redox-state regulator of cells, KCN or $NaN_3$ was used. KCN or sodium azide was prepared immediately before use and used at concentrations described in FIG. 6 or 7, respectively. Two to three plants were placed per a pot (about 40×50 mm) and treatment solution was added dropwise around the shoot apex at 5 ml/day per a pot. KCN or $NaN_3$ treatment was started 17 days after imbibition. The treatments were performed on day 0 (the initiation date of treatment), 1, 3, 5 and 7, which set of treatments was regarded as one processing. The time of floral transition was compared using the rosette leaf number as an index. The experimental results with KCN or $NaN_3$ are shown in FIG. 6 and FIG. 7, respectively. In the figures, 23 cont is the result of water treatment (control experiment). The values are expressed as mean±standard error.

The time of floral transition based on the rosette leaf number was accelerated in the treated group compared with the control group, which was treated with water, at the optimal concentration (KCN: $10^{-3}$; NaN3: $10^{-4}$).

The above results indicate that substances which generate active oxygens have the regulating effect on the floral transition time.

EXAMPLE 4

Regulation of Development at Germination (1)

Figure 8:
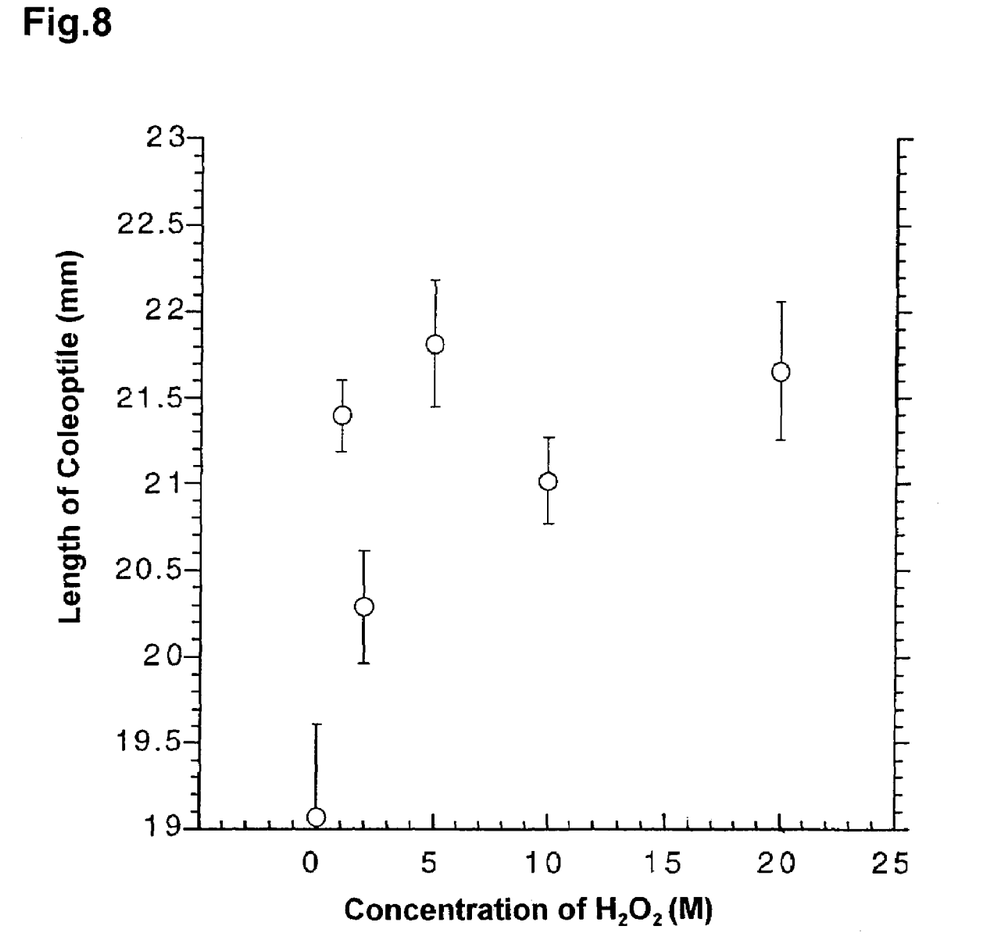
FIG. 8 is a graph showing the regulating effect of hydrogen peroxide on the morphological alteration of Triticum aestivum L. (Regulation of Development (1)). The figure shows the result at 144 hours (6 days) after imbibition. The length of coleoptile treated with each concentration of hydrogen peroxide is depicted. The values are expressed as mean±standard error.

Soft papers were laid in plastic dishes (100×15 mm), and seeded with *Triticum aesivum* L. (cv. Shirasagi) or *Oryza sativa* L. (cv. Nipponbare) (15 seeds/dish). To the dish was added an aqueous solution of hydrogen peroxide up to 15 ml, and allowed to germinate (light condition, 50 µE/m², 16-h light/8-h dark cycle; temperature, *Triticum aesivum* L.: 18° C., *Oryza sativa* L.: 27° C.). Aqueous solutions each containing hydrogen peroxide at the concentrations indicated in FIG. 8 were prepared immediately before use then applied to the seeds. The length of coleoptile of *Triticum aesivum* L. treated with hydrogen peroxide at each concentration was measured at 144 hours (6 days) after imbibition. The results are shown in FIG. 8. In the figure, the values are expressed as mean±standard error.

FIG. 8 shows that the cells were elongated in the plants treated with hydrogen peroxide.

The above results indicate that hydrogen peroxide has the regulatory effect on development involving the cell elongation during the germination period.

EXAMPLE 5

Regulation of Development at Germination (2)

Figure 9:
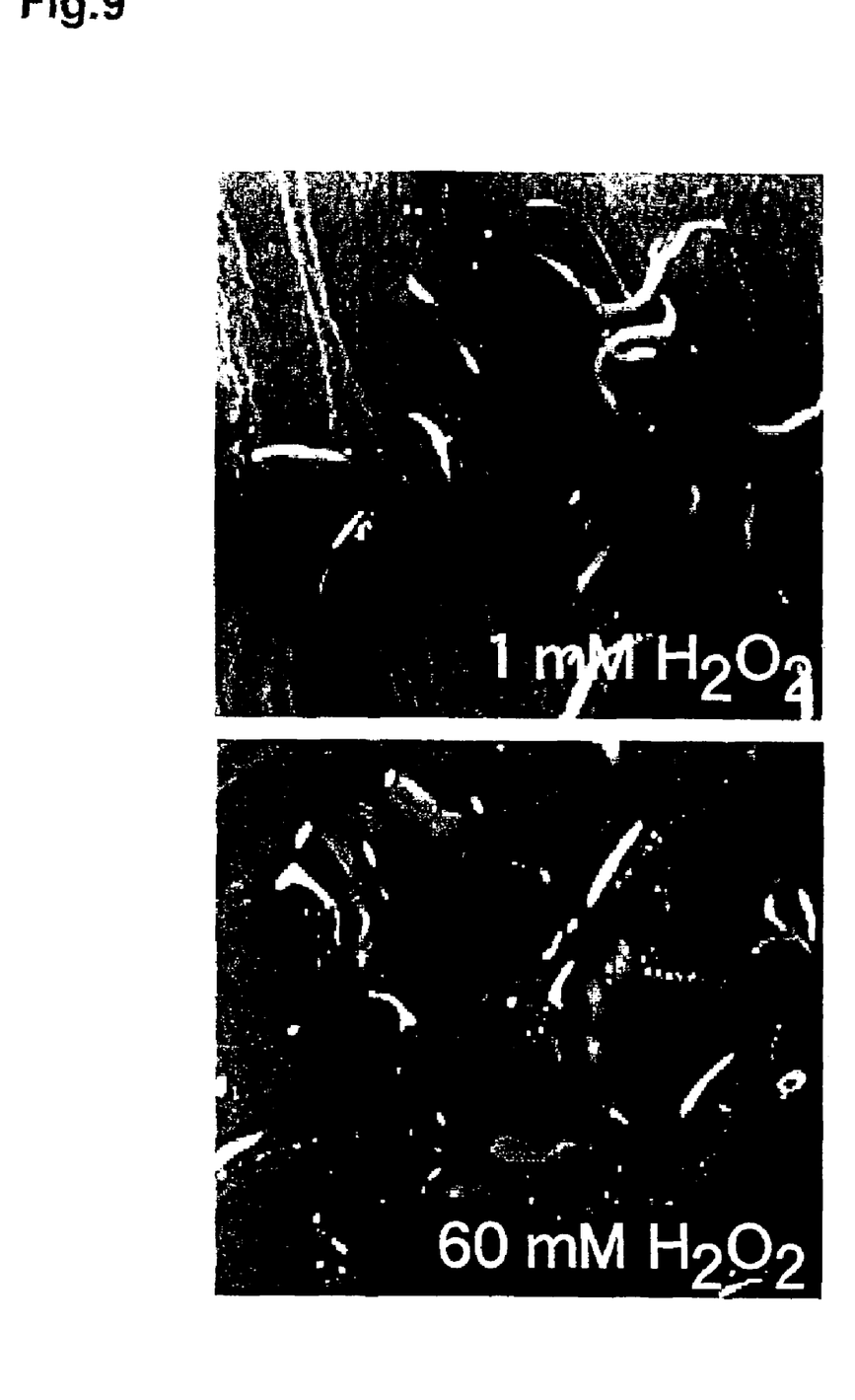

Soft papers were laid in plastic dishes (100×15 mm) and seeded with *Zinnia elegans* L. (cv. Scarlet Frame) (15 seeds/dish). To the dish was added a solution of hydrogen peroxide up to 15 ml, and allowed to germinate (light condition, 50 µE/m², 16-h light/8-h dark cycle; temperature 27° C.). Aqueous solutions each containing hydrogen peroxide at the concentrations indicated in FIG. 9 were prepared immediately before use and applied to the seeds. Observation was performed on 2 days after imbibition (see FIG. 9). In the figure, the concentration of hydrogen peroxide (unit: mM) used in treatment is shown at the right downside of each panel. From the figure showing the germination in the dish treated with 60 mM hydrogen peroxide, it can be seen that cotyledons-opening occurred earlier and that cotyledons came out from the pericarp before root did. Thus, as the concentration of hydrogen peroxide increased, the treated seeds tend to germinate from cotyledon than from root, and the time of cotyledon opening becomes earlier in the treated group compared to the non-treated group.

The above results indicate that hydrogen peroxide has an accelerating effect on the cotyledon opening.

EXAMPLE 6

Regulation of Formation of Adventitious Bud in Callus

The regulatory effect of glutathione on the formation of adventitious buds from callus was examined.

*Nicotina tabacum* L. leaves grown aseptically was callused in a callus-inducible medium (an essential medium consisting of 1% agar and Murashige and Skoog medium (MS medium) supplied with 0.1 mg/L benzyladenine (BA) and 1 ml/L naphthaleneacetic acid (NAA)). The resultant callus was transferred to an adventitious formation medium (an essential medium consisting of 1% agar and Murashige and Skoog medium (MS medium) supplied with 1 mg/L BA and 0.1 ml/L NAA). To the adventitious-formation medium, 0.1 mM BSO, 1 mM GSH or 1 mM GSSG (oxidized glutathione) was added as a redox-state regulator. The same medium lacking in supplements was prepared and used as a control medium. These calli were cultured in the adventitious formation medium or control medium for 3 weeks after induction and the number of adventitious buds was counted. The results are shown in Table 1.

TABLE 1

Regulation of the formation of adventitious bud with glutathione

| Redox-state regulator | GSH | GSSG | BSO | None (control) |
|---|---|---|---|---|
| Adventitious buds/callus | 2-3 | 2-3 | 30 or more | 4-8 |

The above results show that it is possible to control the formation of adventitious buds by artificially changing the amounts and/or redox ratio of glutathione.

EXAMPLE 7

Regulation of Root Hair Formation (1)

Soft papers were laid in plastic dishes (100×15 mm) and seeded with *Arabidopsis thaliana* wild type plant Ler. To the dish was added 15 ml of an aqueous solution of hydrogen peroxide ($10^{-3}$M) for imbibition. Germination was allowed to arise at 23° C. and the root hair formation was observed 1 week after imbibition under a microscope. The root hair formation was recognized in the dish treated with water and not in the dish treated with hydrogen peroxide solution.

EXAMPLE 8

Regulation of Root Hair Formation (2)

Soft papers were laid in plastic dishes (100×15 mm) and seeded with *Glycine max* (cv: Tanbaguro). To the dish was added 15 ml of an aqueous solution of hydrogen peroxide ($10^{-3}$M) for imbibition. Seeds were germinated at 23° C. and the root hair formation was observed at 1 week after imbibition under a microscope. The root hair formation was recognized in the dish treated with water and not in the dish treated with hydrogen peroxide solution.

EXAMPLE 9

Regulation of Tracheary Element Formation

Figure 10:
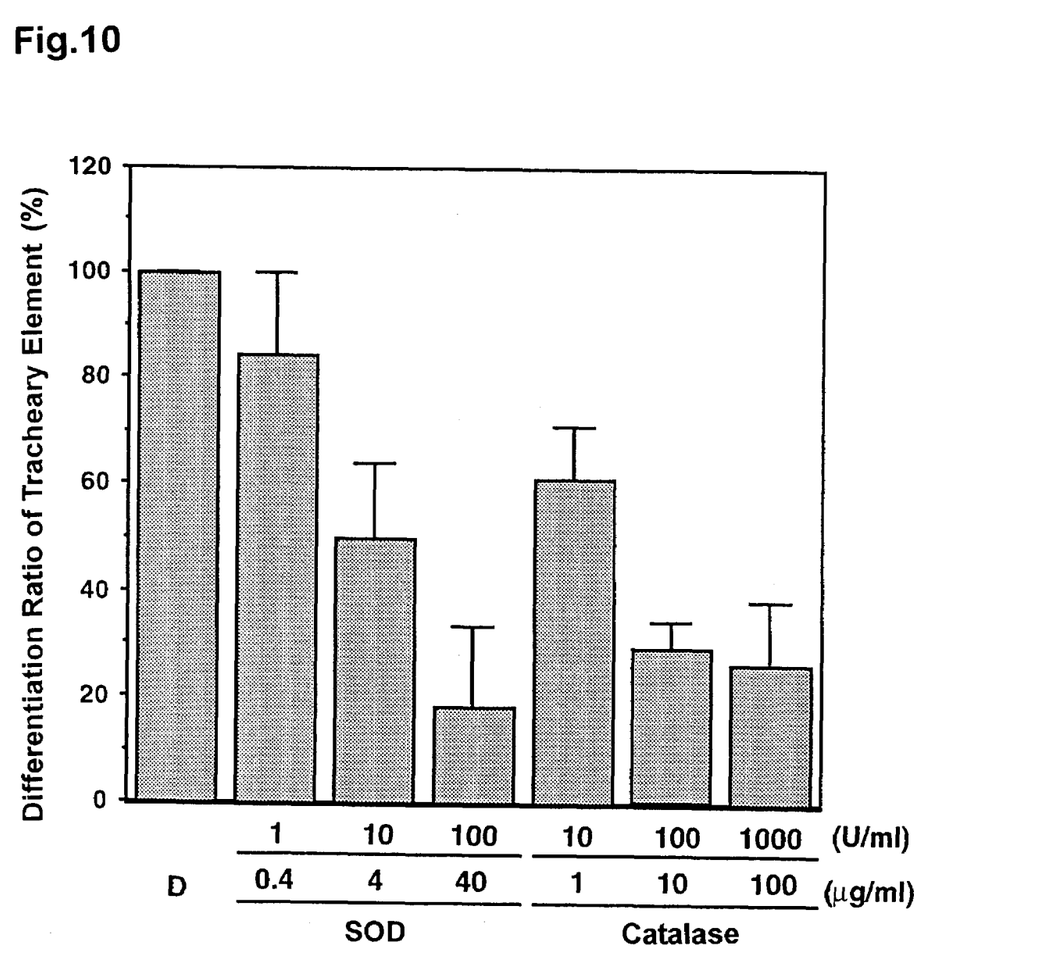
FIG. 10 is a graph showing the results of examination of regulatory effect on the tracheary element differentiation of mesophyll cells cultured in the presence of superoxide dismutase or catalase in the medium. The mesophyll cells were isolated from the 3.5-cm to 4.5-cm-long primary leaves of *Zinnia elegans* (c.v. Canary Bird), which had been grown for 14 days after seeding, and then cultured in the presence of superoxide dismutase (SOD) or catalase in a test tube and subjected to the examination. The concentrations of SOD and catalase added at the start of cultivation is shown at the bottom of column in the activity and protein amount. In the figure, TE stands for the tracheary element. The values are expressed as mean±standard error.

*Zinnia elegans* L. (cv: Canary Bird) was seeded and grown for 14 days, when mesophyll cells were isolated from the 3.5-4.5 cm primary leaves and suspended into a D medium containing naphthalene acetate (0.1 mg/l) and benzylaminopurine (1 mg/l) at $2.5$-$4.0 \times 10^6$/ml. This culture solution (2 ml each) was dispensed into test tubes and subjected to rotary culture at 25° C. in the dark. Superoxide dismutase or catalase was added to the test tube at the concentrations indicated in FIG. 10 at the start of culture. After 72-hour-culture, samples were obtained. Those cells with stripe due to the secondary cell wall thickening were identified as cells differentiated to tracheary elements. The proportion of tracheary-element cells to the total cells was defined as differentiation rate. The result is shown in FIG. 10. In FIG. 10, the vertical axis shows the tracheary element differentiation ratio (TE differentiation)(%). The concentration of SOD or catalase added at the start of culture is shown below the column in the activity (U/ml, upper line) and protein mass (μg protein/ml, lower line). The values are expressed as mean±standard error. In the figure, TE means tracheary element and "D" means D medium.

INDUSTRIAL APPLICABILITY

The present invention enables to regulate the differentiation of a cell or an organ regardless of the category of organism.

The invention claimed is:

1. A method of modifying the flowering time of a plant, which comprises the steps of:
   (1) applying an effective amount of a substance that affects the synthesis or amount of glutathione in cells to the plant, wherein the substance that affects the synthesis or amount of glutathione in cells is selected from the group consisting of glutathione synthesis inhibitors, glutathione derivatives, and substances capable of generating these substances in cells;
   (2) cultivating the plant under conditions suitable for growth at least until the flowering time of the plant; and
   (3) comparing the flowering time of the plant to a control plant to indicate that the flowering time of the treated plant is modified.

2. The method according to claim 1, wherein the substance that affects the synthesis or amount of glutathione in cells is selected from the group consisting of buthionine sulfoximine, methionine sulfoximine, reduced glutathione, oxidized glutathione, homoglutathione, carboxypropylglutathione and dicarboxyethylglutathione.

3. The method according to claim 1, wherein the effective amount of the substance that affects the synthesis or amount of glutathione in cells is applied to a seed or plant body of the plant in step (1).

4. The method according to claim 1, wherein the effective amount of a substance that affects the synthesis or amount of glutathione in cells is applied to a shoot apex or root of the plant in step (1).

5. The method according to claim 1, wherein the substance that affects the synthesis or amount of glutathione in cells is selected from the group consisting of buthionine sulfoximine and glutathione.

6. The method according to claim 1, wherein the substance that affects the synthesis or amount of glutathione in cells is administered once at any stage of cultivation of the plant.

* * * * *